(12) United States Patent
Mikkaichi

(10) Patent No.: US 10,076,381 B2
(45) Date of Patent: Sep. 18, 2018

(54) METHOD OF MARKING LESION IN TUBULAR ORGAN OF AN OBJECT

(71) Applicant: Olympus Corporation, Tokyo (JP)

(72) Inventor: Takayasu Mikkaichi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 904 days.

(21) Appl. No.: 14/479,690

(22) Filed: Sep. 8, 2014

(65) Prior Publication Data
US 2016/0066983 A1 Mar. 10, 2016

(51) Int. Cl.
*A61B 18/14* (2006.01)
*A61B 18/00* (2006.01)

(52) U.S. Cl.
CPC ............ *A61B 18/1492* (2013.01); *A61B 2018/00494* (2013.01); *A61B 2018/00589* (2013.01); *A61B 2018/00595* (2013.01); *A61B 2018/00601* (2013.01); *A61B 2018/00708* (2013.01)

(58) Field of Classification Search
CPC ...... A61B 18/1492; A61B 2018/00494; A61B 2018/0025; A61B 2018/00244; A61B 2018/00833; A61B 2018/00315
See application file for complete search history.

(56) References Cited

U.S. PATENT DOCUMENTS

| 6,044,846 A * | 4/2000 | Edwards ............... A61N 1/056 128/898 |
| 2006/0276784 A1 | 12/2006 | Miyajima et al. |
| 2008/0027429 A1* | 1/2008 | Oyatsu ............... A61B 18/1492 606/45 |
| 2009/0254085 A1 | 10/2009 | Yamamoto |
| 2013/0231646 A1* | 9/2013 | Noar ..................... A61B 18/02 606/14 |

FOREIGN PATENT DOCUMENTS

| JP | A-2006-326157 | 12/2006 |
| JP | A-2008-29667 | 2/2008 |
| WO | WO 2008/026689 A1 | 3/2008 |

* cited by examiner

*Primary Examiner* — Jaymi Della
*Assistant Examiner* — Tigist Demie
(74) *Attorney, Agent, or Firm* — Oliff, PLC DA

(57) ABSTRACT

A method used to mark a tubular organ of a subject. In a first step, at a position near a lesion on a wall surface of the tubular organ, a first electrode is supplied with high-frequency current, so that the first electrode punctures the wall surface from a surface of a mucosal layer on the wall surface to a predetermined depth. In a second step, the first electrode is supplied with the high-frequency current for a predetermined time such that a first marking is made by cauterization on a muscle layer. In a third step, a second electrode, which is disposed coaxially with the first electrode, is supplied with high-frequency current for a predetermined time such that a second marking is made by cauterization on the surface of the mucosal layer. During the third step, the first electrode is held as is after the second step.

14 Claims, 8 Drawing Sheets

METHOD OF MARKING LESION IN TUBULAR ORGAN OF AN OBJECT

BACKGROUND OF THE INVENTION

Field of the Invention

The present invention relates to a method for marking a tubular organ that is present inside a subject. In particular, the present invention is a method for simultaneously making markings for a procedure in substantially the same positions on the interior and exterior of a tubular organ. The markings are made by way of a therapeutic tool channel of an endoscope that is inserted through a natural orifice of the subject.

Description of the Related Art

Various techniques have been conventionally used to make markings for surgery on a tubular organ.

For example, when the interior of a tubular organ is observed under an endoscope and a lesion is found, a marking is made so as to surround the lesion. In other words, a marking device is pressed against a desired position on the periphery of the lesion. The area is then pressed outward while performing cauterization. At the same time, a similar marking is made on the exterior of the tubular organ in the area that bulges as a result of being pressed. This operation is performed repeatedly in a plurality of locations so as to surround the lesion. As a result, a plurality of markings that surround the lesion can be made on the interior and exterior wall portions of the tubular organ. Therefore, the marking positions on the exterior of the tubular organ provide positional information of the lesion that has been visually confirmed on the luminal-side wall of the tubular organ. For example, a procedure, such as excision along the positions on the organ, is performed based on the positional information.

However, several issues that have yet to be improved in the above-described marking method have been noted. One issue is that, when the markings are made on the interior and exterior of the tubular organ (referring to the interior and the exterior with the organ wall therebetween), first, the inner wall (mucosal wall) is marked. Then, the bulging area is marked. In other words, there is a time lag between the interior and the exterior. Therefore, the amount of time required for marking is an issue. In addition, the organ is pressed from the inner side by a tool and made to bulge. The marking position is visually estimated from the shape of the hump shape on the exterior caused by the bulge. Therefore, an issue has been noted in that the accuracy of the marking position on the outer side decreases. This issue is not only caused by the visual estimation. This issue is also often caused by the layers within the organ wall shifting as a result of the organ wall being pressed. The mucosal membrane and the muscle layer are loosely fixed together by a submucosal layer. Therefore, when the inner wall of the organ is pressed, the mucosal layer and the muscle layer become released from the fixed state (i.e., shift). The position on the bulging muscle layer is shifted from the intended marking position. As a result, a positional misalignment occurs between the position of the marking made on the exterior of the organ and the intended marking position.

Furthermore, a plurality of operators (doctors and the like) are required to work in cooperation to mark the interior and exterior of the tubular organ. When the timings do not match among the operators, the amount of time required for marking increases. This results in greater burden placed on the body of the patient.

Specific techniques for making such markings are described in patent literature. For example, WO08/0265689 discloses, as one example, marking the periphery of a lesion at a predetermined interval using a high-frequency knife. The high-frequency knife has a needle-shaped tip. In addition, JP-A-2006-326157 also discloses forming a hole, or in other words, a marking in a portion of the mucosal layer near a lesion using a needle-shaped high-frequency knife. The hole is formed as an incision for circumferential incision.

SUMMARY OF THE INVENTION

In light of the above-described marking methods, it is required that a tubular organ be marked for surgery by a single operator in a short amount of time with good working efficiency.

In an exemplary embodiment, there is provided a method of making a tubular organ of a subject for a treatment thereof, comprising steps of: a contacting step for placing a first electrode in contact with a mucosal layer at a position surrounding a lesion that is observed inside a lumen of the tubular organ and placing a second electrode in contact with a muscle layer, the first and second electrodes being supplied with high-frequency current and disposed coaxially with each other, the mucosal layer forming a part of the tubular organ, the muscle layer forming a part of the tubular organ: and a marking step for marking the mucosal layer and the muscle layer by supplying the high-frequency current to the first and second electrodes.

In another exemplary embodiment, there is provided a method of making a tubular organ of a subject for a treatment thereof, comprising steps of: a first step for puncturing a position near a lesion that is observed on a wall surface inside a lumen of the tubular organ, by a first electrode supplied with high-frequency current, the first electrode puncturing the wall surface from a surface of a mucosal layer on the wall surface to a predetermined depth; a second step for supplying the first electrode with the high-frequency current for a predetermined amount of time such that a first marking is made by cauterization on a muscle layer that is positioned on the outer side of the mucosal layer; and a third step for supplying a second electrode with high-frequency current for a predetermined amount of time such that a second marking is made by cauterization on the surface of the mucosal layer, during which the first electrode is held as is after the second step, the second electrode being disposed coaxially with the first electrode.

Further, in another exemplary embodiment, there is provided a method of making a tubular organ of a subject for a treatment thereof, comprising steps of: an accessing step for making first and second electrodes access a lesion that is observed on a surface of a lumen of the tubular organ, the first and second electrodes being disposed coaxially with each other and being supplied with differing high-frequency currents; a first marking step for marking on the surface of the lumen by cauterization, by placing the second electrode the surface of the lumen at a position near the lesion and by supplying the high-frequency current to the second electrode for a predetermined amount of time; a puncturing step for making the first electrode puncture a muscle layer by making the first electrode advance to the muscle layer during which the first electrode is held in contact with the surface and is supplied with the high-frequency current; and a second marking step for marking the muscle layer by cauterization, by stopping supply of the high-frequency current to the second electrode and holding a puncturing state of the first electrode for a predetermined amount of time.

DETAILED DESCRIPTION OF THE PREFERRED EMBODIMENTS

A preferred example of a method for marking a tubular organ inside a subject (also referred to, hereinafter, as a marking method) of the present invention will hereinafter be described with reference to the drawings.

This marking method is performed by using a therapeutic tool channel in an insertion portion of an endoscope. The insertion portion is inserted through a natural orifice of the subject so as to reach a tubular organ inside the body of the subject. A therapeutic tool is threaded through the therapeutic tool channel. A marking is made by cauterization using the tip end portion of the therapeutic tool. The markings are made in a plurality of positions in the periphery of a lesion on the tubular organ. The markings are made on the wall surfaces of the tubular organ inside the body cavity. In other words, the markings indicate the same positions on the inside and the outside, in positions near the outer surface of the tubular organ, in addition to the inner surface. In addition, the markings are made so as to surround the lesion. Therefore, for example, an operation to excise the lesion is performed, for example, under a laparoscope using the marking positions as a guide. The marking positions appear discolored to white on the outer surface of the tubular organ. Examples of the tubular organ are the esophagus, stomach, duodenum, colon, and the like.

Figure 1:
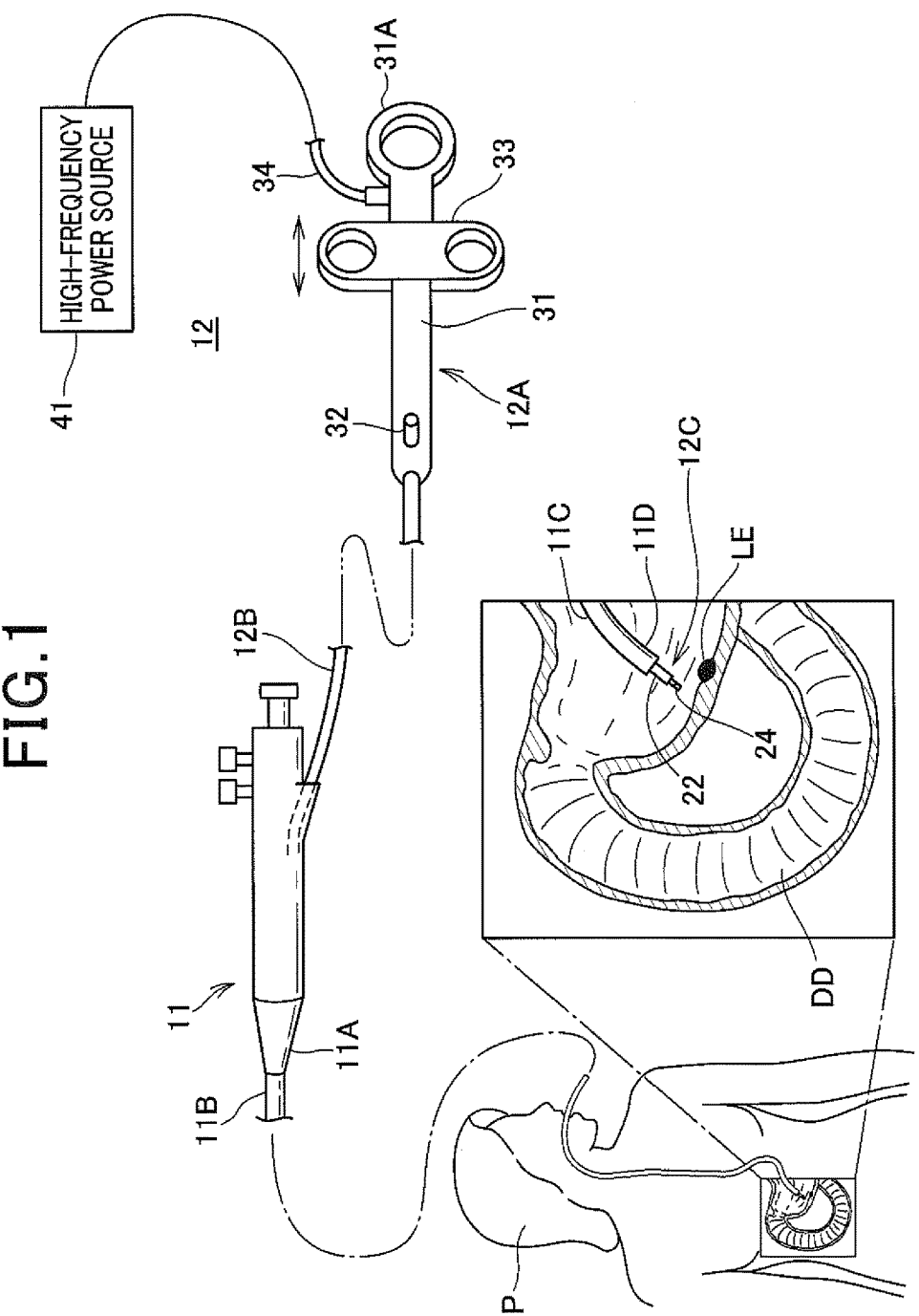
FIG. 1 is a configuration diagram for explaining an overview of a system that performs a marking method of the present invention.

As shown in FIG. 1, the marking method is performed using a flexible endoscope 11 and a marking device 12. The flexible endoscope 11 is orally inserted into the lumen of the subject (patient). The marking device 12 is a therapeutic tool that operates in conjunction with the endoscope 11.

The flexible endoscope 11 has a hand operated portion 11A and an insertion portion 11B. The insertion portion 11*b* is in the form of a thin flexible tube. The hand operated portion 11A and the insertion portion 11B are connected. The insertion portion 11B is provided with a hard tip portion 11D. The hard tip portion 11D is formed integrally with the tip end portion of the insertion portion 11B with a curved portion 11D therebetween. A light, a charge-coupled device (CCD) camera, and the like are attached to the hard tip portion 11D (not shown). Lines pass through the insertion portion 11B and reach the hand operated portion 11A. The lines transmit power and image signals to and from the light, the CCD camera, and the like. In addition, the hand operated portion 11A and the hard tip portion 11D are communicated by various channels, via the insertion portion 11B. The channels include the therapeutic tool channel. As a result, a therapeutic tool (including the marking device, described hereafter) is inserted into the therapeutic tool channel. The therapeutic tool can be used to perform an intended treatment via an endoscope.

The therapeutic tool channel communicates between an opening on the side surface of the hand operated portion 11A and an opening on the front surface of the hard tip portion 11D.

A marking device 12 is inserted into the therapeutic tool channel. The marking device 12 uses cauterization by high-frequency current. Specifically, the marking device 12 includes a hand operated portion 12A, an insertion portion 12B, and a tip electrode portion 12C. The hand operated portion 12A is provided on the hand side, and is held and operated by an operator. The insertion portion 12B is capable of bending freely. The tip electrode portion 12C is provided integrally with the tip end portion of the insertion portion 12. The tip electrode portion 12C also has the same diameter as the tip end portion of the insertion portion 12B. Of these parts, the tip electrode portion 12C and insertion portion 12B section is inserted into the therapeutic tool channel of the endoscope 11.

Figure 2:
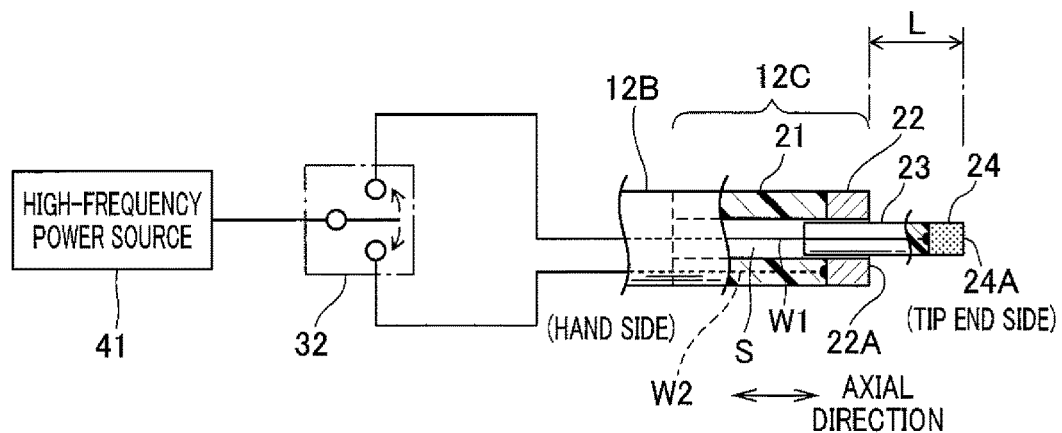
FIG. 2 is an electrical and mechanical explanatory diagram for supplying two electrodes with high-frequency current.

As shown in FIG. 2, the tip electrode portion 12C includes a cylindrical longitudinal member 21 and an electrode 22 (referred to, hereinafter, as a second electrode). The longitudinal member 21 is composed of an electrically insulating material. The longitudinal member 21 is connected integrally with the cylindrical insertion portion 12B. The electrode 22 is composed of a ring-shaped conductive member that has the same diameter as the longitudinal member 21. The electrode 22 is integrally fixed to the tip end side of the longitudinal member 21. The internal space of the longitudinal member 21 is used for the placement of another electrode. Specifically, the tip electrode portion 12C is also provided with a slide member 23 and an electrode 24 (referred to, hereinafter, as a first electrode). The slide member 23 is formed into a thin, elongated columnar shape. The slide member 23 is composed of an insulating material. The slide member 23 is capable of sliding within the internal space S of the longitudinal member 21 along the axial direction thereof. The electrode 24 is composed of a conductive material. The electrode 24 has the same diameter as the slide member 23. The electrode is composed of a conductive material. The electrode 24 is integrally fixed to the tip end portion of the slide member 23.

Figure 3:
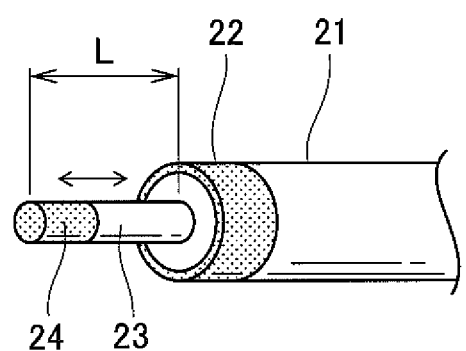
FIG. 3 is a partial perspective view of a tip electrode portion of a marking device.

Therefore, the slide member 23 is capable of sliding within the internal space S of the longitudinal member 21 by a driving mechanism (not shown). The slide member 23 slides back and forth in the axial direction at a fixed stroke L. When the slide member 23 retracts, a tip end surface 24*a* of the first electrode 24 is set to be coplanar with the internal space S, or in other words, the tip end surface 22A of the second electrode 22. In other words, the first electrode 24 enters the internal space of the first electrode 22. Even in this entered state, a fixed clearance is ensured between the two electrodes 24 and 22. In addition, short circuiting does not occur between the two electrodes 24 and 22 by an alternative current supply, as described hereafter. On the other hand, when the first electrode 24 advances, the tip end surface 24A thereof advances by a distance amounting only to the fixed stroke L. FIG. 2 and FIG. 3 show a state in which the first electrode 24 has emerged in this way. In the present example, the movement of the first electrode 24 amounting to the fixed stroke L can be made continuously by manual operation using an operating lever, described hereafter.

Furthermore, a high-frequency current is selectively supplied to the first electrode 24 and the second electrode 22 via conductor wires W1 and W2. When the electrodes 24 and 22 are supplied with the high-frequency current and come into contact with biological tissue, the contact area is cauterized and becomes discolored to white. The white discolored area functions as a marker.

On the other hand, the hand operated portion 12A includes an operation main body 31 that is gripped and operated by the operator. A switch 32 and a slider 33 are mounted on the operation main body 31. Furthermore, the operation main body 31 is provided with an operating portion 31A. The operating portion 31A operates the advancing and retracting of the marking device itself. In addition, the operation main body 31 is connected to a high-frequency power source 41 by a cable 34 (see FIG. 2). Therefore, the high-frequency power source 41 is connected to each of the above-described first and second electrodes 24 and 22 by the above-described conductor wires W1 and W2, via the operation main body 31 (and the switch 32). The switch 32 has three switching positions. The switching positions are a neutral position, a first electrode side position, and a second electrode side position. Therefore, the operator can select power off (cauterization OFF), first electrode 24 ON (cauterization by the first electrode ON), and second electrode 22 ON (cauterization by the second electrode ON) by switching the switch 32.

Furthermore, the high-frequency power source 41 is configured so that the supply modes of high-frequency current to the first electrode 24 differ. For example, the high-frequency power source 41 supplies high-frequency current in cutting mode when the first electrode 24 punctures the organ wall. The high-frequency power source 41 supplies high-frequency current in coagulation mode during marking (cauterization).

Figure 5:
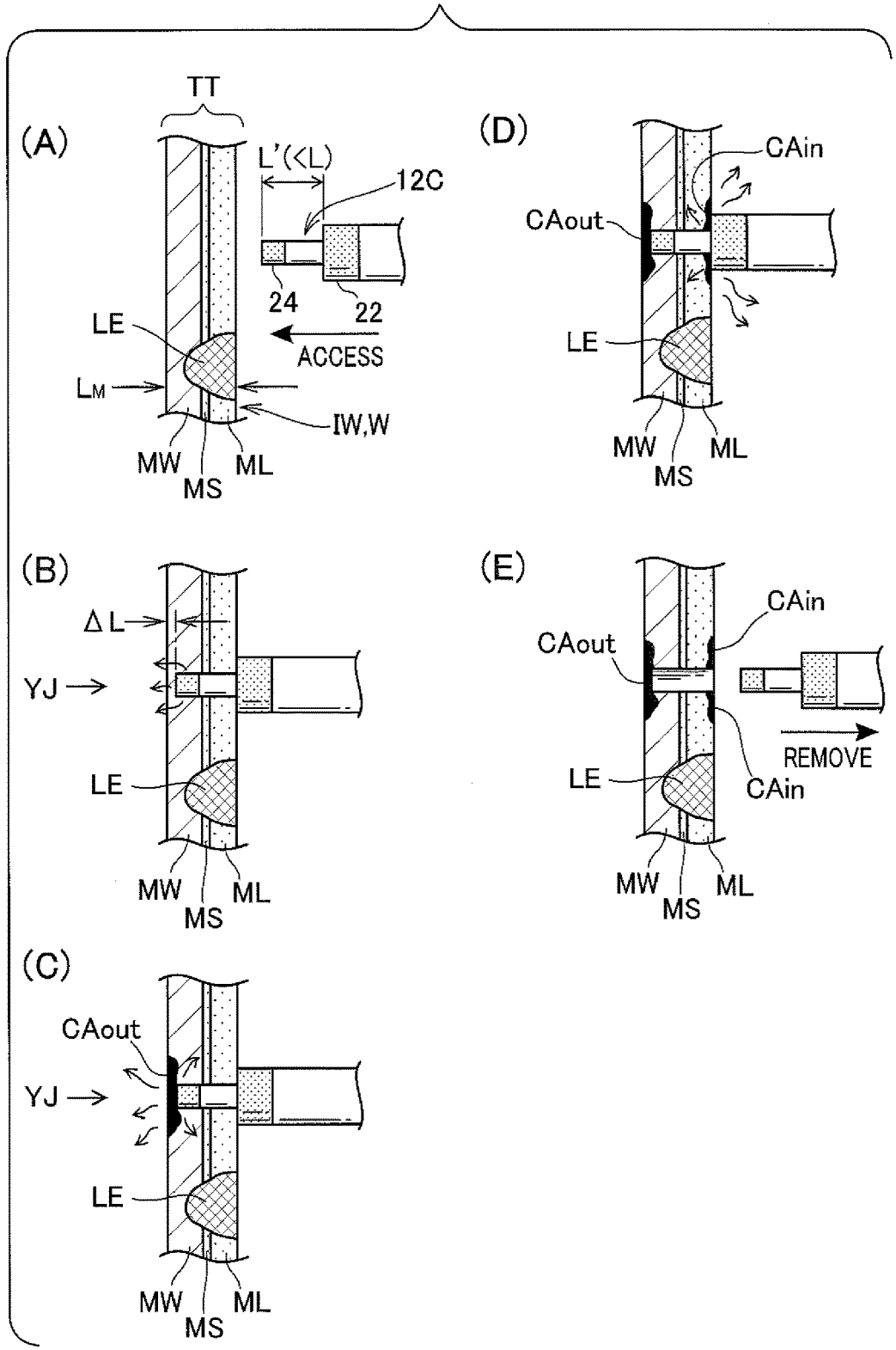
FIG. 5 is an explanatory diagram for explaining the flow for creating a marker that is made by the marking method.
Figure 6:
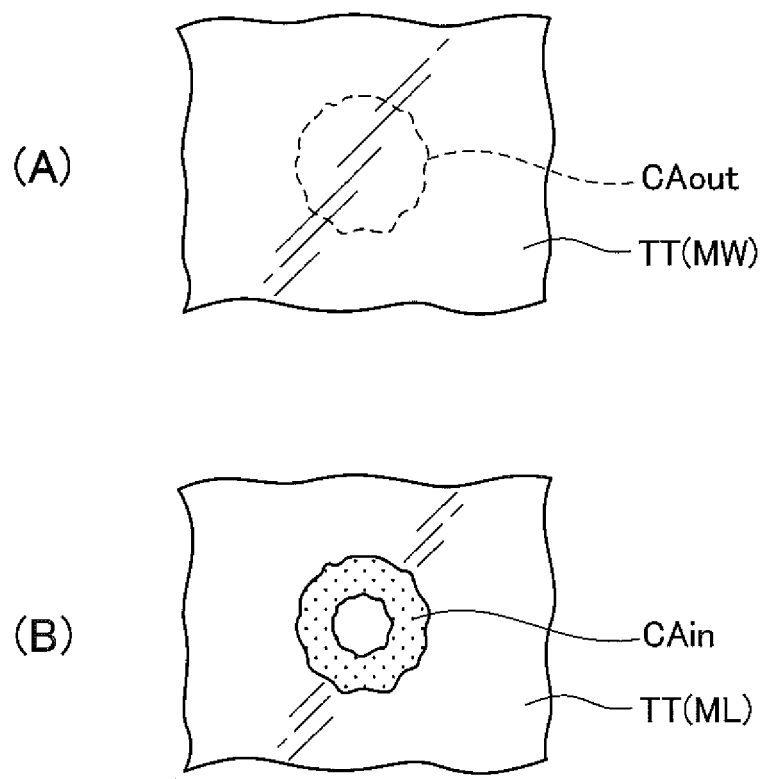
FIG. 6 is a diagram for explaining two types of inner and outer markers that are made.

Next, an example of the marking method according to the present embodiment will be described with reference to FIG. 4 to FIG. 6. The marking is performed by an operator using the endoscope 11 and the marking device 12.

First, the operator presses the operating portion 31 of the marking device 12 against a tubular organ TT (such as the stomach), under an endoscope. The device thereby accesses the inner wall surface IW of the tubular organ TT. In addition, the operator operates the slider 33 and projects the first electrode 24 from the tip electrode portion 12C (see Step S1 in FIG. 4 and FIG. 5(A)). The length of projection is set to L' (<L or =L). The accessed position is one of the target points (marking positions) placed so as to surround a lesion LE that has been observed under the endoscope 11.

The length L1' is a value is set in advance based on the thickness of the wall W of the target tubular organ TT. The thickness is collected by another modality, such as magnetic resonance imaging (MRI) or X-ray computed tomography (CT). The operator may, of course, adjust the projection length L1' on the spot. The wall W of the tubular organ TT ordinarily includes a mucosal layer ML, a submucosal layer SM, and a muscle layer MW, in order from the inner side. In other words, the mucosal layer ML is positioned on the lumen side. The submucosal layer SM is positioned below the mucosal layer ML. The muscle layer MW is loosely joined with the mucosal layer ML with the submucosal layer SM therebetween. According to the present embodiment, the total thickness $L_M$ of the mucosal layer ML and the muscle layer MW (including the submucosal layer SM) at the area to be marked is set to be a value that is $L_M \approx L'$, but slightly $L' < L_M$. However, L' is greater than the thickness of the mucosal layer ML.

From this state, the operator operates the switch 32. The first electrode 24 is supplied high-frequency current in, for example, cutting mode. The switch 32 is set to first electrode ON (Step S2). While in this ON state, the operator operates the operating portion 31A. The operator stabs the tip electrode portion 12C of the marking device 12 towards the inner wall surface IW of the tubular organ TT (Step S3). In accompaniment with this stabbing, the mucosal layer ML, the submucosal layer SM, and the muscle layer MW are cauterized. The projecting first electrode 24 having the length L' punctures both layers ML and MW (including the submucosal layer SM). In addition, the electrode surface 22A of the second electrode 22 comes into contact with the surface of the mucosal layer ML, or in other words, the inner wall surface IW (see the state in FIG. 5(B)). At this time, as shown in FIG. 5(B), the electrode surface 24A of the first electrode 24 has not reached the outer surface of the muscle layer MW. The electrode surface 24A remains within the muscle layer MW with a slight distance ΔL remaining.

Next, from the state in which puncturing has been completed, the operator switches the supply of high-frequency current to, for example, coagulation mode. The operator maintains the first electrode in the ON state for a predetermined amount of time (such as several seconds) (Step S4). As a result, the cauterization at the tip end portion of the first electrode 24 progresses. A cauterized area CAout is formed (see FIG. 5(C)). As schematically shown in FIG. 6(A), the cauterized area is substantially circular or a similar shape when observed from the outer side of the tubular organ U. The cauterized area appears as a white smudge on the surface of the muscle layer MW. Therefore, for example, when observed under a laparoscope from the outer side of the tubular organ TT, the cauterized area is recognized as a whitish marker.

When marking by the first electrode 24 is completed, the supply of current to the first electrode 24 is stopped (Step S5).

Thereafter, the operator switches the switch 32 without moving the tip electrode portion 12C. The operator thereby supplies high-frequency current to the second electrode 22 for a predetermined amount of time (such as several seconds) (Step S6). As a result, at this time, the electrode surface 22A of the second electrode 22 is in contact with the inner wall surface IW, or in other words, the surface of the mucosal layer ML. The surface of the mucosal layer ML is thereby cauterized (see FIG. 5(D)). When this cauterization is completed, the operator stops the supply of current to the second electrode 22 (Step S7).

As schematically shown in FIG. 6(B) for example, a cauterized area CAin formed by the second electrode 22 is a whitish area that is formed into the ring shape of the electrode surface 22A or a similar shape. The cauterized area can be recognized as a marker.

In this way, the two markers CAin and CAout are formed in the same positions on the inner and outer surfaces of the wall W of the tubular organ TT by a single puncture. When this operation is completed, the operator operates the slider 33. The operator removes the first electrode 24 of the tip electrode portion 12C from the tubular organ TT (Step S8). Then, the operator finds the next target point, or in other words, marking position. The operator repeats the above-described operation until a plurality of markers are made so as to surround the lesion LE (Steps S9 and S1.)

In this way, the markers CAin and CAout are each formed in the same position on the inner and outer surfaces of the tubular organ TT, so as to surround the lesion LE. In other words, even when the lesion LE hardly appears on the outer surface of the tubular organ TT, the plurality of markers CAout surround and indicate the lesion LE that is not visible. The markers CAin are formed on the inner surface of the tubular organ TT, or in other words, the luminal surface IW so as to surround the lesion LE that can be observed under an endoscope. Therefore, the excision area of the lesion can be decided based on the markers CAout and CAin on the interior and exterior of the tubular organ. Checking for areas that should be excised but still remain can be performed.

The markings can be made in the same positions on the interior and exterior of the tubular organ with a single puncture. Therefore, various advantages are achieved. Unlike in the past when the markings are made separately for the interior and exterior of the organ, two electrodes that are coaxially arrayed are used. Therefore, the positions in relation to the wall W on the interior and exterior of the organ do not become misaligned. The lesion can be accurately indicated on the interior and exterior of the organ. In addition, the markings on the interior and exterior of the organ can be said to be made almost simultaneously. The markings on the interior and exterior of the organ can be actualized by a single puncture by an electrode. Therefore, reductions in labor and time involved in the puncturing operation can be achieved. Furthermore, coordination between two operators is not required. Complications accompanying the conventional cooperative operation for marking the interior and exterior of the tubular organ do not occur.

In addition, in the marking method according to the present embodiment, the plurality of markers CAout are also made on the outer side of the tubular organ TT. However, holes are not formed on the outer side of the tubular organ TT. The area of the marker CAout remains sealed and is only discolored to a whitish color. Therefore, the burden placed on the subject is also reduced.

Furthermore, the marking method according to the present embodiment differs from the technique in the past. In the past, the inner wall of the organ is pressed and made to bulge. The marking position on the outer wall of the organ is found by the bulge. Unlike this technique, the step of pressing the inner wall of the organ with a tool is not performed. Therefore, positional misalignment between the layers within the wall of the organ is unlikely to occur. As a result, compared to the marking method that uses bulging, high accuracy can be ensured for the markings made on the outer wall of the organ.

Figure 4:
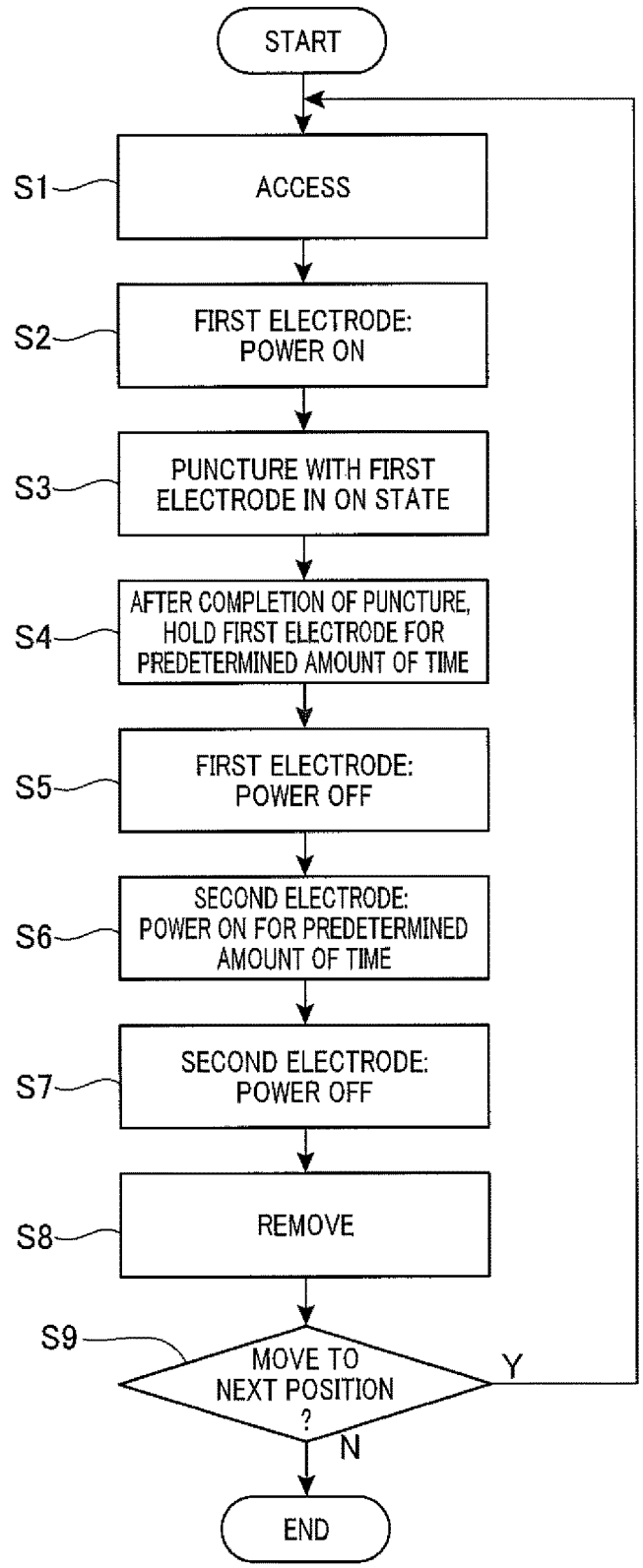
FIG. 4 is a flowchart of a procedure for performing an example of the marking method.

In the above-described procedure of the marking method shown in FIG. 4, the processes at Steps S4 and S5 may be performed in parallel, or in other words, simultaneously with the processes at Steps S6 and S7. As a result, the markers CAout and CAin are formed simultaneously on the interior and exterior of the tubular organ TT. The amount of work time required for marking can be reduced.

VARIATION EXAMPLES

Another example of the above-described marking method will be described with reference to FIG. 7 and FIG. 8.

Figure 7:
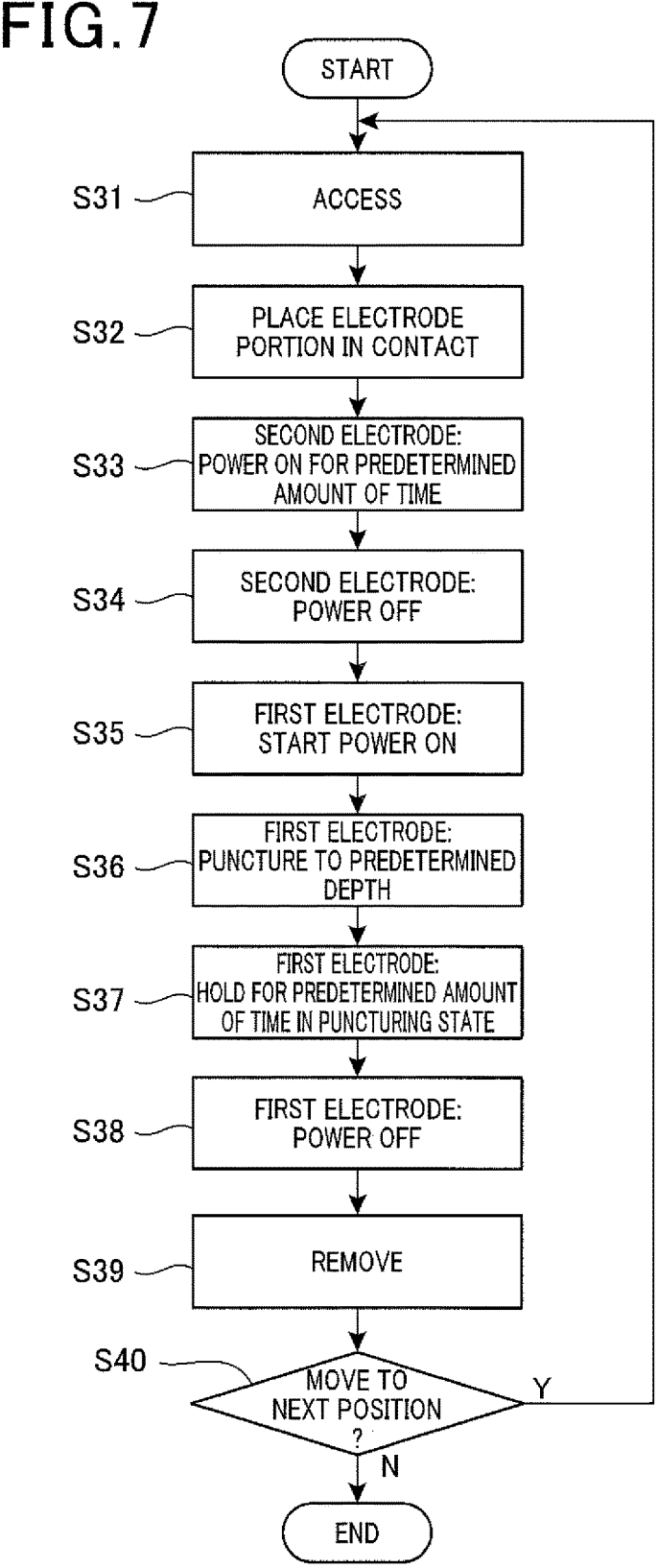
FIG. 7 is a flowchart of a procedure for performing another example of the marking method.
Figure 8:
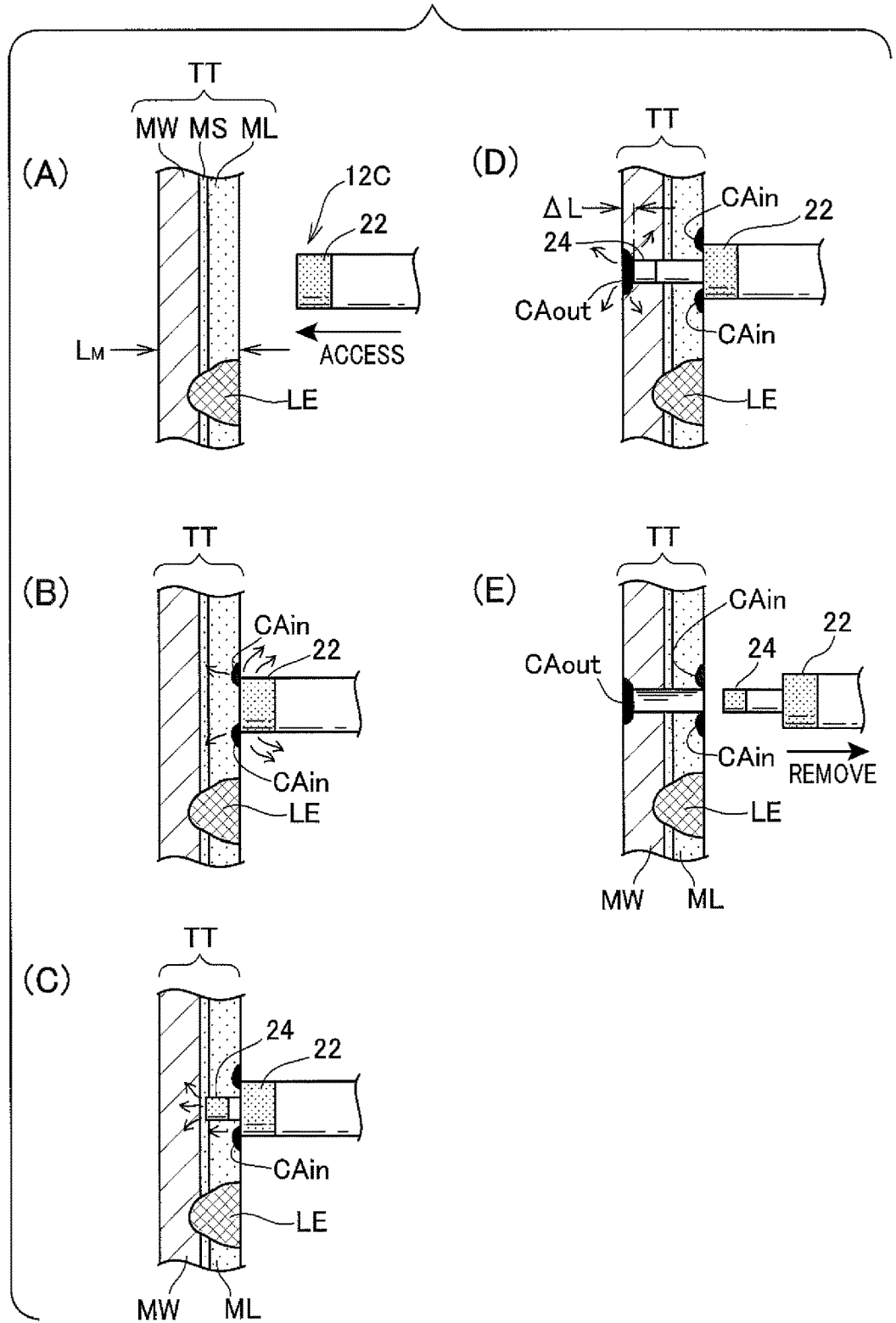
FIG. 8 is an explanatory diagram for explaining the flow for creating a marker that is made by this other marking method.

First, in a manner similar to that described above, the tip electrode portion 12C of the marking device 12 accesses a desired position of the tubular organ TT, or in other words, the target position in the periphery of a lesion (Step 31 in FIG. 7: see FIG. 8(A)). Next, the tip electrode portion 12C is placed in contact in this position (Step S32: see FIG. 8(B)). At this time, the first electrode 24 is inside the internal space of the second electrode 22. The first electrode 24 and the second electrode 22 are positioned coaxially.

In this state, the operator operates the switch 32 and supplies the second electrode 22 with high-frequency current for a predetermined amount of time (such as several seconds) (Step S33).

As a result, in a manner similar to that described above, the inner marker CAin is formed on the luminal surface IW by cauterization (see FIG. 8(C)).

Next, the operator operates the switch 32 and turns off power to the second electrode 22 (Step S34). Furthermore, the operator starts supply of high-frequency current to the first electrode 24 in, for example, cutting mode (Step S35). In this state, the operator uses the slider 33 and slowly advances the first electrode 24 by a predetermined distance L' (Step S36; see FIG. 8(C)). The distance L' is set to be similar to that according to the first embodiment. Then, in the state in which the first electrode 24 has been advanced by the predetermined distance L', the operator switches the high-frequency current to, for example, coagulation mode and waits for a predetermined amount of time (such as several seconds) (Step S37). As a result, in a manner similar to that described above, the outer marker CAout can be made on the outer surface of the tubular organ (see FIG. 8(D)). The outer marker CAout appears whitish on the outer surface of the tubular organ.

When this operation is completed, the operator stops power to the first electrode 24 (Step S38). The operator removes the tip electrode portion 12C (Step S39: see FIG. 8(E)). Furthermore, if there is a next target point, the above-described process is repeated (Steps S40 and S31).

In this way, working effects similar to those of the above-described method can also be achieved by the marking method in the present variation example. As a result, the aspects of the marking method can be diversified.

In addition, the present invention is not limited to the configurations described in the above-described example and variation example. The configurations can be combined with conventionally known configurations and further appropriate configurations can be achieved without departing from the spirit of the invention recited in the scope of claims.

What is claimed is:

1. A method of marking a tubular organ of a subject for a treatment thereof, comprising the steps of:
   placing a first electrode of an instrument in contact with a mucosal layer of the tubular organ at a position closely surrounding a lesion that is observed inside a lumen of the tubular organ and placing a second electrode of the instrument in contact with a muscle layer of the tubular organ, the muscle layer being adjacent to the mucosal layer, the first and second electrodes being configured to be supplied with high-frequency current and disposed coaxially with each other; and
   marking the mucosal layer and the muscle layer by supplying the high-frequency current to the first and second electrodes.

2. The method of marking a tubular organ of a subject for a treatment thereof according to claim 1, further comprising the step of:

observing the marking on the muscle layer by using a laparoscope inserted in an abdominal cavity.

3. A method of marking a tubular organ of a subject for a treatment thereof, comprising the steps of:
marking surface of a mucosal layer of the tubular organ by causing cauterization of the mucosal layer by a first electrode of an instrument supplied with high-frequency current, the first electrode puncturing a position near a lesion observed on a wall surface inside a lumen of the tubular organ, wherein the wall surface comprises the surface of the mucosal layer; and
marking a first surface of a muscle layer of the tubular organ by causing cauterization of the muscle layer by a second electrode of the instrument supplied with high-frequency current, the second electrode being disposed coaxially with the first electrode.

4. The method of marking a tubular organ of a subject for a treatment thereof according to claim 3, further comprising the step of:
puncturing the position near the lesion that is observed inside the lumen of the tubular organ by the first electrode of the instrument supplied with high-frequency current, the first electrode penetrating from the mucosal layer of the tubular organ into the muscle layer of the tubular organ, the muscle layer being adjacent to the mucosal layer;
wherein the step of marking the mucosal layer comprises causing cauterization by the second electrode of the instrument supplied with the high-frequency current when the first electrode is puncturing the surface of the mucosal layer.

5. The method of marking a tubular organ of a subject for a treatment thereof according to claim 4, further comprising the step of:
observing the marking on the muscle layer by using a laparoscope inserted in an abdominal cavity.

6. The method of claim 4, wherein the high-frequency current that causes the cauterization of the muscle layer marking step is different from the high-frequency current that causes the cauterization of the mucosal layer marking step.

7. The method of claim 6, wherein the high-frequency current supplied to the first electrode in the muscle layer marking step is in a cutting mode and the high-frequency current supplied to the second electrode in the mucosal layer marking step is in a coagulation mode.

8. The method of claim 4, wherein, in the muscle layer marking step, the first electrode punctures the muscle layer while the high-frequency current is being supplied to the first electrode, and during the puncturing of the muscle layer, the high-frequency current is not supplied to the second electrode.

9. The method of claim 8, wherein the muscle layer marking step and the mucosal layer marking step are performed in sequence or substantially in parallel to each other.

10. The method of claim 8, wherein the first electrode has a circular tip end surface which is placed in contact with the muscle layer, and the second electrode has an annular tip end surface which is placed in contact with the surface of the mucosal layer.

11. The method of claim 4, wherein the first electrode punctures the muscle layer to a predetermined depth, the predetermined depth being set to a depth which enables a tip end of the second electrode to penetrate a second wall surface of the muscle layer but stop short of the first surface of the muscle layer.

12. The method of claim 4, comprising stopping the supply of the high-frequency current to the second electrode after the mucosal marking step and removing the first and second electrodes from the wall surface of the tubular organ.

13. A method of marking a tubular organ of a subject for a treatment thereof, the tubular organ having a mucosal layer adjacent to a muscle layer, comprising the steps of:
cutting through the mucosal layer and a surface of the muscle layer adjacent to the mucosal layer with a first electrode of an instrument, until an end surface of the first electrode is within the muscle layer and a second electrode of the instrument is in contact with a surface of mucosal layer that is spaced from the muscle layer, the first and second electrodes being co-axial;
using the first electrode to cauterize the surface of the muscle layer which is spaced from the mucosal layer; and
using the second electrode to cauterize the surface of the mucosal layer which is spaced from the muscle layer.

14. The method of marking a tubular organ of a subject for a treatment thereof according to claim 13, further comprising the step of:
observing the marking on the muscle layer by using a laparoscope inserted in an abdominal cavity.

* * * * *